US012559299B2

(12) United States Patent　　　　　(10) Patent No.:　US 12,559,299 B2
Johansson　　　　　　　　　　　　　　(45) Date of Patent:　Feb. 24, 2026

(54) PACKAGE FOR DRILLS, A METHOD AND AN ARRANGEMENT THEREFORE

(71) Applicant: DENTSPLY SIRONA Inc., York, PA (US)

(72) Inventor: Henrik Johansson, Partille (SE)

(73) Assignee: Dentsply Sirona Inc., York, PA (US)

( * ) Notice: Subject to any disclaimer, the term of this patent is extended or adjusted under 35 U.S.C. 154(b) by 183 days.

(21) Appl. No.: 18/122,167

(22) Filed: Mar. 16, 2023

(65) Prior Publication Data

US 2023/0219741 A1　　　Jul. 13, 2023

Related U.S. Application Data

(63) Continuation of application No. 16/451,945, filed on Jun. 25, 2019, now abandoned, which is a (Continued)

(30) Foreign Application Priority Data

May 8, 2012　(EP) ..................................... 12167150

(51) Int. Cl.
　　B65D 85/20　　　(2006.01)
　　A61B 50/30　　　(2016.01)
　　　　　　　(Continued)

(52) U.S. Cl.
　　CPC .............. B65D 85/20 (2013.01); A61B 50/30 (2016.02); A61C 3/04 (2013.01); A61C 19/02 (2013.01); B65D 25/105 (2013.01); B65D 85/24 (2013.01)

(58) Field of Classification Search
　　CPC ...... B65D 85/20; B65D 25/105; B65D 85/24; A61B 50/30; A61C 3/04; A61C 19/02
　　　　　　　(Continued)

(56) References Cited

U.S. PATENT DOCUMENTS

| 3,010,569 A | | 11/1961 | Goldman | |
| 4,005,776 A | * | 2/1977 | Seeley ................... | B65D 75/52 |
| | | | | 206/364 |

(Continued)

FOREIGN PATENT DOCUMENTS

| DE | 19715030 A1 | 10/1998 |
| DE | 10146905 A1 | 7/2003 |

(Continued)

OTHER PUBLICATIONS

"U.S. Appl. No. 13/862,643, Examiner Interview Summary mailed Apr. 4, 2017", 2 pgs.

(Continued)

*Primary Examiner* — Jacob K Ackun
(74) *Attorney, Agent, or Firm* — SCHWEGMAN LUNDBERG & WOESSNER, P.A.

(57)　　　　　ABSTRACT

The invention relates to a package for a drill. The package has a protecting portion arranged to house a cutting portion of said drill in a contact free manner and a locking portion arranged to hold a tool engaging portion of said drill. The locking portion and the protecting portion are movable relative each other and the drill is releasable from the locking portion by a movement of the locking portion relative the protecting portion. The protecting portion is allows the user to clamp the cutting portion of said drill by pressing the protecting portion and thereby establishing a contact between the protecting portion and the cutting portion of said drill. The invention also relates to a method and an arrangement.

10 Claims, 3 Drawing Sheets

Related U.S. Application Data continuation of application No. 13/862,643, filed on Apr. 15, 2013, now abandoned.

(60) Provisional application No. 61/643,945, filed on May 8, 2012.

(51) Int. Cl.
| | |
|---|---|
| *A61C 3/04* | (2006.01) |
| *A61C 19/02* | (2006.01) |
| *B65D 25/10* | (2006.01) |
| *B65D 85/24* | (2006.01) |

(58) Field of Classification Search
USPC ................................................. 206/349, 363
See application file for complete search history.

(56) References Cited

U.S. PATENT DOCUMENTS

| | | | | | |
|---|---|---|---|---|---|
| 4,413,731 | A | * | 11/1983 | Weideman | B65D 85/20 |
| | | | | | 206/583 |
| 4,445,611 | A | * | 5/1984 | Shofu | B65D 85/24 |
| | | | | | 206/820 |
| 4,909,386 | A | * | 3/1990 | Jeffers | B25H 3/003 |
| | | | | | 206/379 |
| 5,533,625 | A | * | 7/1996 | Mikkelsen | B25H 3/003 |
| | | | | | 206/755 |
| 6,540,073 | B1 | * | 4/2003 | Hagel | B65D 75/305 |
| | | | | | 206/467 |
| 6,923,327 | B1 | | 8/2005 | Cohen | |
| 8,079,487 | B2 | | 12/2011 | Roesler | |
| 2006/0283769 | A1 | * | 12/2006 | Roesler | B65D 85/20 |
| | | | | | 206/349 |
| 2007/0138043 | A1 | * | 6/2007 | Roesler | B25H 3/003 |
| | | | | | 206/379 |
| 2008/0135445 | A1 | | 6/2008 | Juliano | |
| 2011/0056850 | A1 | * | 3/2011 | Guenter | B65D 25/101 |
| | | | | | 206/63.5 |
| 2011/0192746 | A1 | * | 8/2011 | Chang | B65D 25/22 |
| | | | | | 206/379 |
| 2013/0299371 | A1 | * | 11/2013 | Johansson | B65D 25/105 |
| | | | | | 206/349 |
| 2019/0315563 | A1 | | 10/2019 | Johansson | |
| 2023/0157780 | A1 | * | 5/2023 | Moloney | A61B 34/37 |
| | | | | | 206/349 |

FOREIGN PATENT DOCUMENTS

| | | | |
|---|---|---|---|
| DE | 102005022385 | A1 | 11/2006 |
| DE | 102007005515 | B3 | 8/2008 |
| DE | 202011105720 | U1 | 11/2011 |
| EP | 2662312 | A1 | 11/2013 |
| EP | 2662312 | B1 | 10/2014 |
| WO | WO-2013167353 | A1 | 11/2013 |

OTHER PUBLICATIONS

"U.S. Appl. No. 13/862,643, Examiner Interview Summary mailed May 2, 2017", 2 pgs.
"U.S. Appl. No. 13/862,643, Final Office Action mailed May 26, 2016", 12 pgs.
"U.S. Appl. No. 13/862,643, Final Office Action mailed Jun. 19, 2018", 8 pgs.
"U.S. Appl. No. 13/862,643, Non Final Office Action mailed Aug. 24, 2015", 13 pgs.
"U.S. Appl. No. 13/862,643, Non Final Office Action mailed Aug. 31, 2017", 9 pgs.
"U.S. Appl. No. 13/862,643, Notice of Non-Compliant Amendment mailed Jan. 11, 2017", 3 pgs.
"U.S. Appl. No. 13/862,643, Notice of Non-Compliant Amendment mailed Jun. 25, 2014", 3 pgs.
"U.S. Appl. No. 13/862,643, Notice of Non-Compliant Amendment mailed Dec. 27, 2018", 3 pgs.
"U.S. Appl. No. 13/862,643, Response filed Feb. 23, 2016 to Non Final Office Action mailed Aug. 24, 2015", 7 pgs.
"U.S. Appl. No. 13/862,643, Response filed Feb. 26, 2018 to Non Final Office Action mailed Aug. 31, 2017", 7 pgs.
"U.S. Appl. No. 13/862,643, Response filed Mar. 17, 2014 to Restriction Requirement mailed Jan. 15, 2014", 6 pgs.
"U.S. Appl. No. 13/862,643, Response filed Apr. 26, 2017 to Notice of Non-Compliant Amendment mailed Jan. 11, 2017", 8 pgs.
"U.S. Appl. No. 13/862,643, Response filed Oct. 22, 2014 to Notice of Non-Compliant Amendment mailed Jun. 25, 2014", 6 pgs.
"U.S. Appl. No. 13/862,643, Response filed Nov. 28, 2016 to Final Office Action mailed May 26, 2016", 8 pgs.
"U.S. Appl. No. 13/862,643, Response filed Dec. 17, 2018 to Final Office Action mailed Jun. 19, 2018", 7 pgs.
"U.S. Appl. No. 13/862,643, Restriction Requirement mailed Jan. 15, 2014", 7 pgs.
"U.S. Appl. No. 16/451,945, Final Office Action mailed Sep. 16, 2022", 10 pgs.
"U.S. Appl. No. 16/451,945, Notice of Non-Compliant Amendment mailed Mar. 21, 2023", 3 pgs.
"U.S. Appl. No. 16/451,945, Response filed Mar. 15, 2023 to Final Office Action mailed Sep. 16, 2022", 8 pgs.
"U.S. Appl. No. 16/451,945, Response filed Jun. 1, 2022 to Restriction Requirement mailed Dec. 15, 2021", 5 pgs.
"U.S. Appl. No. 16/451,945, Restriction Requirement mailed Dec. 15, 2021", 7 pgs.
"European Application Serial No. 12167150.7, Extended European Search Report mailed Aug. 27, 2012", 6 pgs.
"European Application Serial No. 12167150.7, Response filed Mar. 10, 2014 to Extended European Search Report mailed Aug. 27, 2012", 44 pgs.
"International Application Serial No. PCT/EP2013/057857, International Search Report mailed Jul. 18, 2013", 5 pgs.
"International Application Serial No. PCT/EP2013/057857, International Preliminary Report on Patentability mailed Nov. 20, 2014", 8 pgs.
"International Application Serial No. PCT/EP2013/057857, Written Opinion mailed Jul. 18, 2013", 6 pgs.

* cited by examiner

PACKAGE FOR DRILLS, A METHOD AND AN ARRANGEMENT THEREFORE

CROSS-REFERENCE TO RELATED APPLICATIONS

This patent application is a continuation of U.S. Ser. No. 16/451945 filed Jun. 25, 2019 which a continuation of U.S. Ser. No. 13/862,643 filed on Apr. 15, 2013 which claims the benefit of and priority to EP Application Ser No. 12167150.7, filed on May 8, 2012 and U.S. Provisional Patent Application Ser. No. 61/643,945, filed on May 8, 2012, which are herein incorporated by reference for all purposes.

TECHNICAL FIELD OF THE INVENTION

The present invention relates to a package for a drill, such as a surgical drill, e.g. a dental drill. The invention also relates to an arrangement comprising a drill and such package. Furthermore, the invention relates to a method for releasing a drill from such package. The invention also relates to a method for connecting a drill held in such package to a tool holding fixture.

BACKGROUND OF THE INVENTION:

Drills, such as dental drills, should be protected from impacts since the sharp edges of the drill are easily impaired. Furthermore, dental drills need to be kept in a sterile environment until shortly before use. The cutting region of the drill (i.e. the bit) is especially associated with high demands of sterility. Therefore there are high demands on the drill's packaging.

During insertion of the drill into, for example, a tool holding fixture, the handling of the drill's package is important since it is cumbersome to release the drill from the package without touching the drilling bit. Progress in the field of packages for drills has led to the possibility to insert the drill into a tool holding fixture without touching the bit.

DE-A-102005022385 discloses an individual packaging case for objects with fracture risk. This packaging case comprises a base with an open, upward-pointing receiving bore, into which the shank of the object with fracture risk is inserted and self-containedly protrudes from the bore. The fragile particle is protected by means of a protective cap. Further, the packaging case is foldable over an axis running perpendicular to the longitudinal axis and due to the folding, the object to be protected becomes at least partly freely accessible.

A problem with this kind of packaging case is that it needs to be very clean in order to prevent contamination of the object since the cutting edges of the drill is not fastened to the package in a contact free manner. Unless the drill is properly arranged in the package, there may be a risk of the drill wobbling and repeatedly impinging against the package during transport and handling of the package. In such case, the drill may be contaminated by particles of the packaging material which may become cut away and subsequently be transferred with the drill into the oral cavity of a patient, which is undesirable.

A solution to this problem is disclosed in US2011/0056850 where a package housing for an elongate object is disclosed. This package housing includes a base element having a housing wall. The base element comprises a head part and a holding part connected to each other by a weakening zone, the latter is a predetermined breaking zone.

The holding part includes a holding portion which is intended to hold the object in the holding part. The holding portion includes a spacer such that the object can be held in a contact-free manner with respect to the housing wall.

However this type of package housing has a rather complicated construction and the industry is in need of further packaging improvements entailing an easy connection of the drill to a tool holding fixture.

SUMMARY OF THE INVENTION

An object of the invention is therefore to overcome the above problems, and to provide a package for a drill which is easy to handle during the connection of the drill to a tool holding fixture.

This and other objects, which will become apparent in the following, are accomplished by means of a package, an arrangement and methods defined in the accompanying claims.

The present invention is based on the insight that a cutting portion of a drill may be held out of contact from the package until the time of installation of the drill into a tool holding fixture, at which time a user may clamp the cutting portion of the drill with the package to hold and guide the drill into the tool holding fixture. In other words, repeated impinging of the drill against the package is avoided while allowing a controlled one-time gripping of the drill, which is not believed to cause the above mentioned cutting-away of packaging material. Compared to the prior art, this results in an easier handling during the installation of the drill into a tool holding fixture, while still maintaining a satisfactory level of sterility and patient safety.

In particular, the inventor has realized that if while clamping the cutting portion of the drill, release of the drill from its package can easily be accomplished if the part of the package securing a tool engaging portion of the drill, i.e. a locking portion of the package, is moved relative the protecting portion of the package. Hereafter the drill can be inserted into a tool holding fixture in an easy manner and with full control of the user.

According to at least a first aspect of the invention, a package for a drill is provided. The package comprises a protecting portion comprising a first subportion and a second subportion, the protecting portion being arranged to house a cutting portion of said drill in a contact free manner, and a locking portion arranged to hold a tool engaging portion of said drill, wherein the locking portion and the protecting portion are movable relative each other, wherein the drill is releasable from the locking portion by a movement of the locking portion relative the protecting portion, and wherein the first and the second subportions of the protecting portion are made in one piece and are arranged to allow the user to clamp the cutting portion of said drill by pressing the first subportion towards the second subportion and thereby establishing a contact between the protecting portion and the cutting portion of said drill.

When the user fixates the drill by pressing the first and/or the second subportion(s) of the protecting portion an easy connection of the drill to a tool holding fixture is possible, without the need for the user to touch the cutting portion of the drill. The user may fixate the drill after the drill has been released from the locking portion. However, the user may fixate the drill prior to the releasing movement of the locking portion, which is advantageous since the clamping fixation of the cutting portion facilitates the release of the drill from the locking portion when the locking portion is moved relative to the protecting portion.

It should be understood that the cutting portion is the part of the drill not being the tool engaging portion of the drill. The cutting portion generally comprises the sharp edges of the drill (the bit), which can be located along the longitudinal axis of the drill or perpendicular to the axis of the drill or located in another direction, while the tool engaging portion generally comprises the shank of the drill. Furthermore, the drill and the tool holding fixture are two different objects. The drill is here defined as the object used for creating a bore hole and being in direct contact with the matter cut or pressed away, while the tool holding fixture is the equipment to which the drill is to be connected. The tool holding fixture may be a drilling apparatus used by e.g. a dentist.

The protecting portion has at least two functions, one being to house the cutting portion of the drill in a contact-free manner, thereby avoiding sharp edges from contact with the package during storage and transport. This ensures that the drill is kept away from possible contaminations. A second function is to provide a portion allowing the user to clamp the drill by pressing the outer surface of that portion. It should be noted that the protecting portion may house only a part of the cutting portion of the drill. However, the protecting portion may also completely house the cutting portion of the drill.

As mentioned previously, the locking portion and the protecting portion are movable relative each other. Hereby the drill can be released from the locking portion by fixing the drill in the protecting portion and subsequently, or prior to fixing the drill in the protecting portion, establishing a movement of the protecting portion relative the locking portion. This is advantageous since it entails easy handling of the drill upon connection of the drill to a tool holding fixture. In other words, the package can be regarded as having two drill fixating portions. One drill fixating portion would be the locking portion which is intended to initially fixate the drill during storage. The other one would be the protecting portion which is intended to temporarily fixate the drill by manual force while the drill is connected to a tool holding fixture. Thus, the package according to the invention allows for a change from the locking portion's non-manual fixation of the drill to the protecting portion's manual fixation of the drill.

As mentioned previously, the first subportion is made in one piece with the second subportion of the protecting portion, i.e. they are integral with each other. The protecting portion may, for instance, be made by injection moulding or vacuum forming. According to at least one example embodiment, the second subportion is a continuation of the first subportion, without any intermediate portion there between. According to at least one example embodiment, the first subportion and the second subportion are connected by means of a distal package portion, the distal package portion being a continuation of the first subportion and the second subportion being a continuation of the distal package portion.

According to at least one example embodiment, the protecting portion is made in one piece with the locking portion. Hereby, the protecting portion and the locking portion may, for instance, be made by injection moulding or vacuum forming. According to at least one example embodiment, the whole package is made in one piece by e.g. injection moulding or vacuum forming.

According to at least one example embodiment, the package is an inner package adapted to be contained in an outer package. Thus, the inner package may be sterilized together with the drill while the outer surface of the outer package may be non-sterile. The outer package may then also assure sterility by protecting the drill and its inner package from outer contamination.

According to at least one example embodiment, the movement of the locking portion relative the protecting portion while the cutting portion of the drill is clamped results in the release of the tool engaging portion of the drill from the locking portion. According to at least one example embodiment, the movement of the locking portion, and thus the release of the drill, occurs prior to the clamping of the cutting portion of the drill. This may be achieved by the package itself, for instance, during the movement of the locking portion the drill may become tilted so that the cutting portion abuts the walls of the protecting portion. Hereby a counterforce, similar to when clamping the drill, is exerted on the drill by the walls of the package, thus allowing for the release of the drill with the continued relative movement between the locking portion and the protecting portion.

According to at least one example embodiment, at least one of the first and the second subportions of the protecting portion is made from a flexible material. According to at least one example embodiment, other parts of the package are made from a flexible material. The flexible material may be plastic, but it may also be other materials, such as rubber, paper or thin metal foil. By having the drill's package at least partly made from a flexible material, the drill may be stored out of contact from the package and then clamped at will. The installation procedure is especially facilitated if the portion of the package protecting the cutting portion of the drill, e.g. the first and the second subportions of the protecting portion, is made from a flexible material. In this case, a user is allowed to fixate the drill by clamping the protecting portion.

By having the package at least partly made in a flexible material, bending and compressing the package is possible, while a non-flexible part of the package may provide for increased rigidity and stability of the package. For example, two different parts of the package may be made from a flexible material. The first flexible part may be a part of the protecting portion which enables the user to clamp the drill in the before mentioned manner, while the second flexible part may allow for the movement between the protecting portion and the locking portion, e.g. by a bending movement. The remaining parts of the package may be made from a non-flexible material. Hereby, the risk for a part of the package to flex back is reduced. Also, having parts of the package made from a non-flexible material reduces the risk of the package prematurely coming into contact with the sharp edges of the drill.

It should be understood that the term flexible here implies that a user may bend or flex the parts being flexible. Thus, a package may still be made in one piece, where some portions are made thicker, e.g. so thick that the user cannot bend or flex such portions (i.e. not flexible portions) with his/her fingers while some portions are made thinner, e.g. thin enough for a user to bend or flex such portions (i.e. flexible portions) with his/her fingers. In other words, the package may be made partly flexible.

Further, by constructing at least a part of the package in a flexible material, such as plastic, a cheap and functional package may be made. Also using plastic material facilitates the manufacturing process since the package may be produced by injection moulding, vacuum forming etc.

It should be noted that the user may clamp the protecting portion and thereby establish a contact between the package and at least a part of the drill by other means than having the package at least partly made from a flexible material. For instance, the first subportion may be allowed to be moved towards the second subportion by means of a hinge. Hereby the first and the second subportions of the protecting portion may be rigidly constructed.

According to at least one example embodiment the protecting portion has a U-shaped cross-section around the cutting portion of the drill. The first and second subportions of the protecting portion form the two legs of the U-shape. Suitably, distally of the cutting portion of the drill a space is formed between the drill and the central connecting distal package portion of the "U-shape" of the package.

According to at least one example embodiment the first and second subportions are formed as elongated legs. According to other example embodiments the first and second subportion may have other shapes, for instance, the shape of a square. Such shapes may be advantageous, for instance, for accommodating several drills arranged in parallel with each other and held by respective locking portions.

According to at least one example embodiment, the locking portion comprises a snap lock. The use of a snap lock is advantageous since it is possible to integrate the locking means with the remaining package. Hereby also the manufacturing process is facilitated since a snap lock is possible to produce by injection moulding. A snap lock is further advantageous since it may be designed strong enough for holding the drill securely during storage and transport, and yet weak enough to enables the drill to be released using a relatively small force. However, the use of a snap lock does not limit the invention, the drill could be fastened by other means, such as a mechanical lock. For example, the mechanical lock may contain the tool engaging portion of the drill by means of a foldable cap. Unfolding the cap from the engaging portion of the drill may then result in the release of the drill from the package.

According to at least one example embodiment, the package is adapted such that the movement of the locking portion relative the protecting portion may be achieved by bending the package. Hereby, the relative movement between the locking portion and the protecting portion is carried out in a simple manner. The bending movement is especially suitable for sections of the package made from a flexible material.

According to at least one example embodiment, the package is adapted such that the relative movement between the locking portion and the protecting portion may be achieved by pivoting the locking portion around an axis that is perpendicular to the longitudinal axis of the package. According to at least one example embodiment, the package is adapted such that the relative movement between the locking portion and the protecting portion may be achieved by pivoting the locking portion around the longitudinal axis of the package. It should be understood that the function of the relative movement between the locking portion and the protecting portion is to release the drill from the locking portion. This could be achieved by any other suitable type of relative movement between the locking portion and the protecting portion.

According to at least one example embodiment, the package further comprises a gripping portion located adjacent the locking portion. The gripping portion has the advantage that it facilitates handling of the package by allowing the user to hold a specific part of the package. This is advantageous for example when the user removes the package from an outer package and also when the user removes the drill from the package. Hereby, the user can avoid unintentional touching of the drill.

The word adjacent does here imply that the gripping portion is located in close proximity of the locking portion. According to at least one example embodiment, the gripping portion is located opposite the protecting portion such that the locking portion is located between the gripping portion and the protecting portion. According to at least one example embodiment, the gripping portion is juxtapositioned the locking portion. According to at least one example embodiment, the gripping portion is designed such that it is integrated with the locking portion. According to yet another example embodiment the gripping portion is located between the locking portion and a distal end of the protecting portion.

According to at least one example embodiment, the gripping portion is designed as a lip. Hereby the user can easily grip the lip by using a thumb and another finger. This type of grip is advantageously when the user removes the inner package from the outer package and also when the user removes the drill from the package.

According to at least one example embodiment, the package is adapted such that the relative movement between the locking portion and the protecting portion may be achieved by a movement of the gripping portion away from the longitudinal axis of the package. Hereby the drill can be released from the locking portion by for example bending the package.

According to at least a second aspect of the invention, a method is provided for releasing a drill from a package comprising a protecting portion housing a cutting portion of the drill in a contact free manner and a locking portion holding a tool engaging portion of the drill, the method comprising the steps of: clamping the drill by pressing the protecting portion; releasing the drill from the locking portion by moving the locking portion relative the protecting portion while maintaining the clamping of the drill.

Effects and features of this second aspect of the present invention are largely analogous to those described above in connection with the first aspect. For instance, the package may partly be made in a flexible material and/or be made in one piece.

According to at least one example embodiment, a method is provided wherein the movement of the locking portion relative the protecting portion is achieved by bending the package.

According to at least one example embodiment, a method is provided wherein the relative movement between the locking portion and the protecting portion is achieved by pivoting the locking portion around an axis that is perpendicular to the longitudinal axis of the package.

According to at least one example embodiment, a method is provided where wherein the package further comprises a gripping portion located adjacent to the locking portion. The relative movement between the locking portion and the protecting portion may thus be achieved by a movement of the gripping portion away from the longitudinal axis of the package.

According to at least a third aspect of the invention a method is provided for connecting to a tool holding fixture a drill held in a package comprising a protecting portion housing a cutting portion of the drill in a contact free manner and a locking portion holding a tool engaging portion of the drill, the method comprising the steps of: releasing the drill from the locking portion by moving the locking portion relative the protecting portion, and clamping the drill by pressing the protecting portion wherein the clamping is performed prior, after or during the step of releasing the drill, and connecting, while maintaining the clamping of the drill, the tool engaging portion of the drill to the tool holding fixture.

Effects and features of this third aspect of the present invention are largely analogous to those described above in connection with the first and second aspects. For instance, the package may partly be made in a flexible material and/or be made in one piece.

According to at least a fourth aspect of the invention an arrangement comprising a package according to the first aspect and a drill is provided. In the arrangement the protecting portion of the package houses a cutting portion of the drill in a contact free manner, and wherein the locking portion of the package holds a tool engaging portion of the drill, and wherein the locking portion and the protecting portion are movable relative each other, and wherein the drill is releasable from the locking portion by a movement of the locking portion relative the protecting portion, and wherein the protecting portion comprises a first subportion and a second subportion arranged to allow the user to clamp the tool engaging portion of the drill by pressing the first subportion towards the second subportion and thereby establishing a contact between the protecting portion and the cutting portion of the drill.

According to at least one example embodiment, the movement of the locking portion relative the protecting portion while the cutting portion of the drill is clamped results in the release of the tool engaging portion of the drill from the locking portion. According to at least one example embodiment, the movement of the locking portion, and thus the release of the drill, occurs prior to the clamping of the cutting portion of the drill. This may be achieved by that the package itself withholds the drill by for example the walls of the protecting portion. Hereby a counterforce, similar to when clamping the drill, is exerted on the drill by the walls of the package, thus allowing for the release of the drill with the relative movement between the locking portion and the protecting portion.

Effects and features of this fourth aspect of the present invention are largely analogous to those described above in connection with the first, second and third aspects. For instance, the package may partly be made in a flexible material and/or be made in one piece.

DETAILED DESCRIPTION OF THE DRAWINGS

Figure 1:
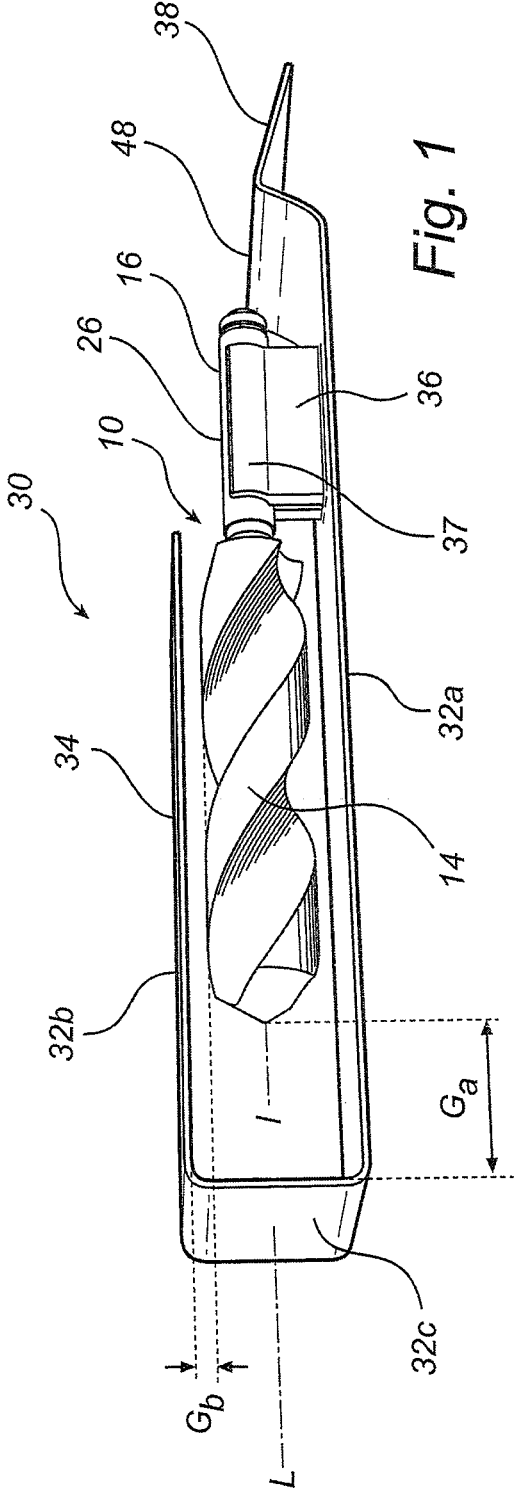
FIG. 1 illustrates an arrangement comprising a drill and a package according to at least one example embodiment of the invention.

FIG. 1 illustrates an arrangement comprising a drill 10 and a package 30 according to at least one example embodiment of the invention.

The package 30 in FIG. 1 comprises a protecting portion 34, a locking portion 36 and a gripping portion 38, wherein the package 30 has a geometrical longitudinal axis L. In the illustrated example, the drill 10 is secured to the locking portion 36 of the package 30 in such manner that its geometrical longitudinal axis I coincides or is parallel with the longitudinal axis L of the package 30.

The protecting portion 34 is arranged to house a cutting portion 14 of the drill 10 in a contact free manner. This is illustrated by a gap Ga located along the longitudinal axis L, and a gap Gb located radially of the longitudinal axis L, both gaps Ga, Gb being defined by the protecting portion 34 and the cutting portion 14 of the drill 10. The protecting portion 34 is substantially U-shaped. The U-shape forms part of first and second subportions in the form of an elongated first leg 32a and an elongated second leg 32b of the package 30, which legs 32a, 32b are linked by a relatively short distal package portion 32c. In the illustrated example embodiment, the first subportion or leg 32a is longer than the second subportion or leg 32b and provides a base from which the locking portion 36 projects. Also, the end of the first leg 32a may be provided with a curve 48 to form the gripping portion 38. The first leg 32a, the second leg 32b and the linking distal portion 32c may all be flexible. Alternatively, it would be conceivable to only have one leg flexible (e.g. the first leg 32a) and the other rigid (e.g. the second leg 32b). Although, the illustrated package 30 is open laterally, in other embodiments it would be conceivable to have one or more lateral sidewalls (33a-33c shown in FIG. 3a-3b), which interconnect the first leg 32a with the second leg 32b similarly to the distal package portion 32c, thus further enclosing/concealing the cutting portion 14 of the drill 10. Furthermore, such lateral sidewalls do not necessarily have to interconnect the legs 32a, 32b, but could for instance extend from the second leg 32b downwards towards but not all the way to the first leg 32a.

The locking portion 36 is arranged to hold the tool engaging portion 16 of the drill 10. In the illustrated example, the locking portion 36 comprises a snap lock 37. Although, the locking portion 36 in FIGS. 1-2 comprises a snap lock 37, locking by other means are possible.

The gripping portion 38 is located adjacent the locking portion 36 and may be constructed in various manners. The gripping portion 38 facilitates the handling of the package 30, for example when removing the package 30 from an outer package (not shown) and when installing the drill 10 into a tool holding fixture 80 (shown in FIG. 2c). In the illustrated example, the gripping portion 38 is designed as a lip. This is advantageous since the user 90 may perform the gripping (indicated with the arrows in FIG. 2a) by using a thumb and another finger (e.g. the indexing finger). In one example embodiment the gripping portion 38 may adjoin the locking portion 36.

When inserting the drill 10 into the package 30, the shaft 26 of the drill 10 is secured to the locking portion 36. In the example embodiments in FIG. 1, this is achieved by that the snap lock 37 in the locking portion 36 first deflects and after the shaft 26 has been placed correctly, elastically springs back. Hereby, a stable and secure locking of the drill 10 is achieved. As mentioned before an outer package may cover the drill 10 and its package 30.

Figures 2A, 2B, 2C:
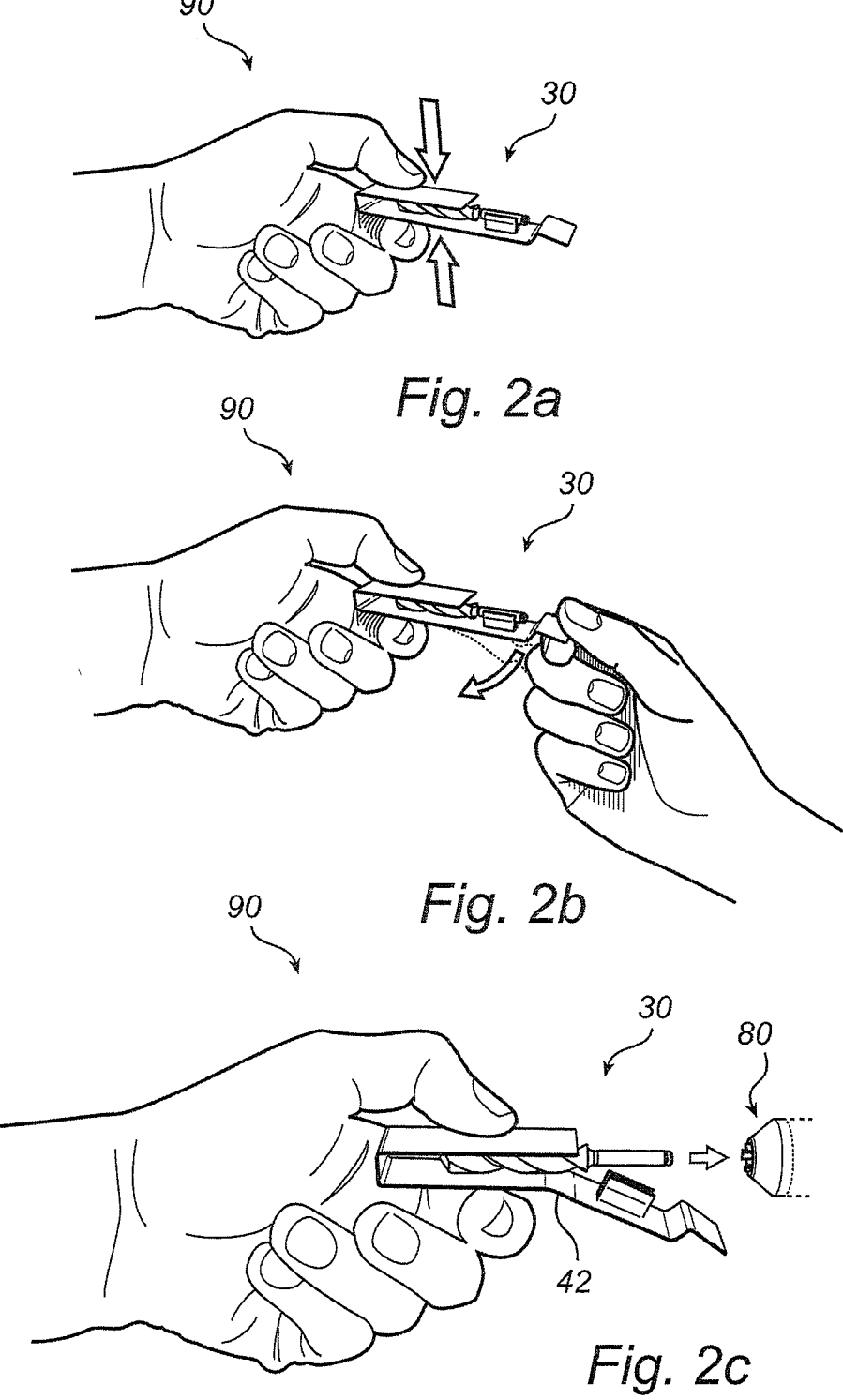
FIGS. 2a-2c schematically illustrates a procedure for releasing a drill from its package and connecting the drill to a tool holding fixture according to at least one example embodiment of the invention.

An example of the process for releasing the drill 10 from the package 30 and connecting the drill 10 to a tool holding fixture 80 is illustrated FIGS. 2a-2c. At least the protecting portion 34 is made from a flexible material thus allowing the user 90 to clamp the cutting portion 14 of the drill 10 by pressing (FIG. 2a) the protecting portion 34 and thereby establishing a contact between the protecting portion 34 and the cutting portion 14 of the drill 10.

As can be seen in FIGS. 2b-2c, the locking portion 36 and the protecting portion 34 are movable relative each other. When the user 90 clamps the flexible protecting portion 34, and thereby establishes a contact between the protecting portion 34 and the cutting portion 14 of the drill 10, a movement (indicated with a curved arrow in FIG. 2b) of the locking portion 36 relative the protecting portion 34 results in the release of the tool engaging portion 16 of the drill 10 as illustrated in FIGS. 2b-2c.

In the examples illustrated in FIGS. 2a-2c, the movement between the locking portion 36 and the protecting portion 34 is possible by means of a bendable portion 42 located somewhere between the locking portion 36 and the distal end 32c of the protecting portion 34. In FIGS. 2a-2c the user 90 clamps the gripping portion 38 and the movement of the locking portion 36 relative the protecting portion 34 is achieved by a movement of the gripping portion 38 away from the longitudinal axis L. Accordingly, in FIGS. 2a-2c, the movement of the locking portion 36 relative the protecting portion 34 is achieved by bending.

In FIGS. 2a-2c the force needed to overcome the holding force of the drill 10 is dependent on the distance between the position where the user 90 clamps the drill 10 and the locking portion 36, and the distance between the locking portion 36 and the position where the user 90 clamps the gripping portion 38.

Although, the movement in FIG. 2b is achievable by means of a bendable portion 42, other alternatives such as a hinge, a mechanical joint or other similar pivoting means are possible.

As seen in FIG. 2b, the movement is achieved by pivoting the locking portion 36 around an axis that is perpendicular to the longitudinal axis L of the package 30. In the drawing, this is illustrated as a downward movement, i.e. opposite to the opening of the snap lock 37, which is facing upwards.

The procedure of releasing the drill 10 can in other words be explained with reference to the fixation of the drill 10 by the three following states:

State 1: The drill 10 is fixed in a first fixing position by the locking portion 36, (the cutting portion 14 of the drill 10 is housed inside the protecting portion 34) as illustrated in FIG. 1.

State 2: The drill 10 is fixed in a first fixing position by the locking portion 36, (the cutting portion 14 of the drill 10 is housed inside the protecting portion 34), and the drill 10 is fixed in a second fixing position by the protecting portion 34 (the user 90 clamps the protecting portion 34) as illustrated in FIGS. 2a-2b.

State 3: The drill 10 is released from the first fixing position by a movement of the locking portion 36 relative the protecting portion 34 while the second fixing position remains unchanged, thus the drill 10 is (only) fixed in the second fixing position by the protecting portion 34 (and is ready to be installed into a tool holding fixture 80) as illustrated in FIG. 2c.

Figure 3A:
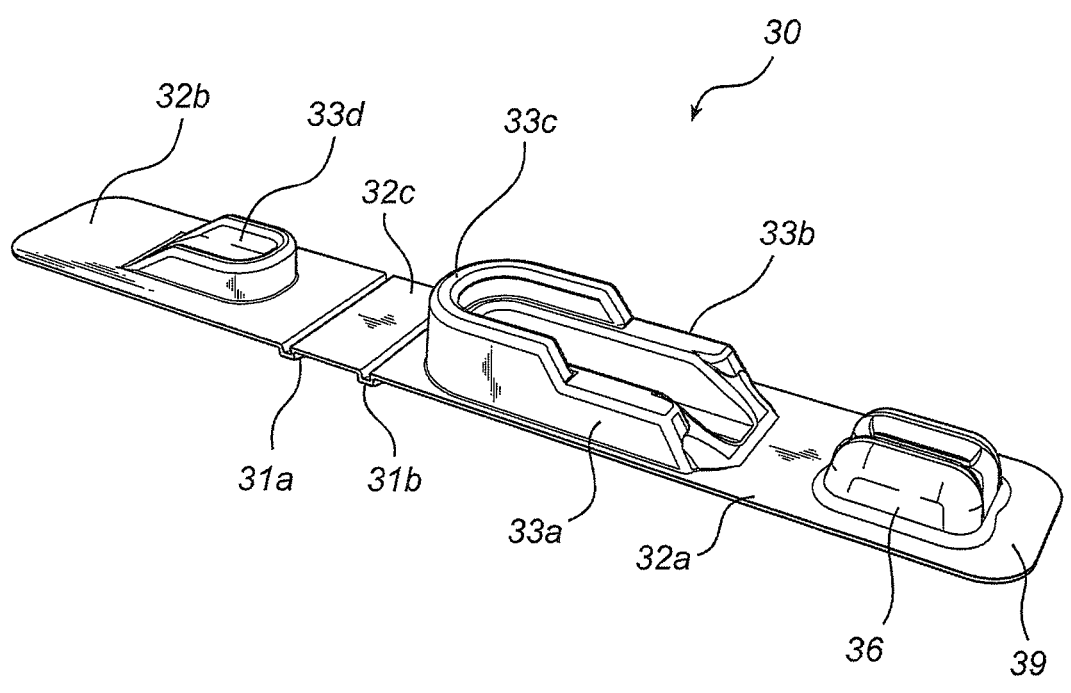
FIGS. 3a-3b schematically illustrates a package according to at least one example embodiment of the invention.
Figure 3B:
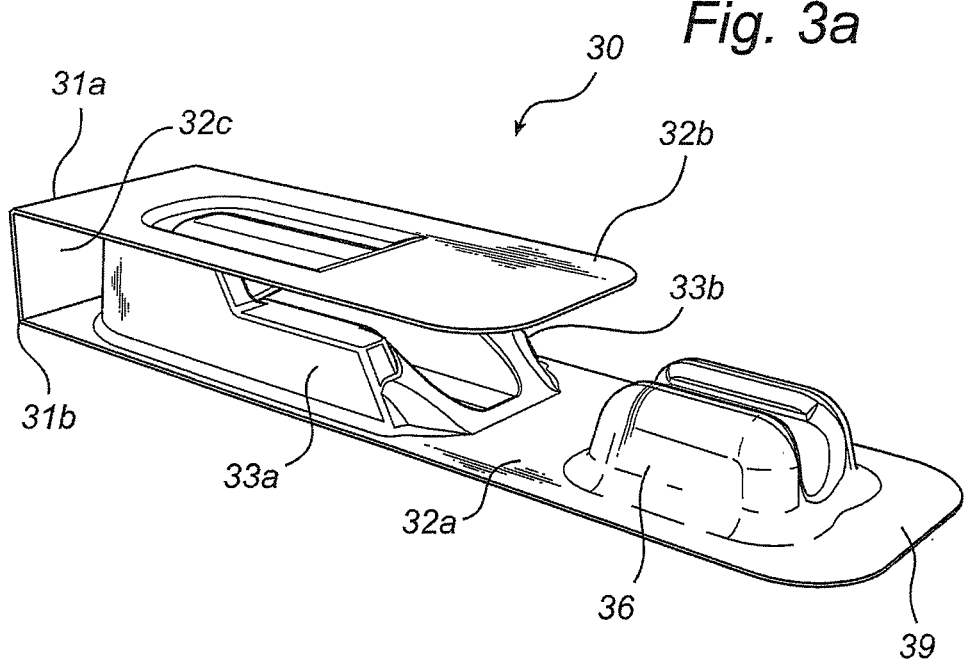

FIG. 3a-3b illustrates a package 30 according to at least one example embodiment of the invention. FIG. 3a shows the package 30 in its unfolded state, i.e. prior to the fixation of the drill to the package 30. FIG. 3b illustrates a state where the package 30 has been folded to enclose the drill (the drill is not shown in FIGS. 3a-3b). Two grooves 31a, 31b are present on both sides of the short distal package portion 32c allowing for the package to be folded.

The example embodiment shown in FIGS. 3a-3b has many similarities to the example embodiments shown in FIGS. 1-2 but with some additional features such as lateral sidewall 33a-33c present between the first leg 32a and the second leg 32b of the package 30. Furthermore, the gripping portion 39 and the locking portion 36 are designed a bit differently compared to the example embodiments shown in FIGS. 1-2.

In FIG. 3a the lateral sidewalls 33a, 33b extends from the first leg 32a and are linked to each other by a distal sidewall 33c, also extending from the first leg 32, such that a U-shaped sidewall is formed. The U-shaped sidewall is designed to enclose the drill. Furthermore, in FIGS. 3a-3b a U-shaped connection part 33d extends from the second leg 32b. The connection part 33d is designed to interconnect with the lateral sidewalls, 33a-33c, thus allowing the second leg 32b to be held to the first leg 32a, as shown in FIG. 3a. In the illustrated example, the interconnection between the connection part 33d and the sidewalls 33a-33c is achieved by means of a snapping function. Of course the lateral sidewalls 33a-33c and the connection part 33d may be interconnected by other means than a snapping function. Furthermore, the lateral sidewalls 33a-33c and the connection part 33d may adopt other designs than the U-shape form exemplified here.

Release of the drill 10 due to a movement of the locking portion 36 relative the protecting portion 34 is in the example embodiment shown in FIGS. 2a-2c possible by that the user 90 fixates the drill 10 by clamping the protecting portion 34. In an alternative embodiment, the release of the drill 10 may be performed prior to clamping the drill 10. This may be achieved by moving the locking portion 36 relative the protecting portion 34, so that the package 30 itself withholds the drill 10 by for example the first 32a or the second leg 32b of the U-shaped protecting portion 34. Preferably, one or more lateral sidewalls (33a-33c shown in FIGS. 3a-3b), which interconnect the first leg 32a with the second leg 32b are provided in the protecting portion 34. Hereby, after the drill 10 is released from the locking portion 36, the drill 10 may be contained inside the package 30 without being fixated. Connection of the drill 10 to a tool holding fixture 80 is then possible by the before mentioned clamping of the drill 10 by pressing a flexible part of the protecting portion 34.

The person skilled in the art realizes that the present invention by no means is limited to the embodiments described above. For instance, although the drawings have only illustrated packages containing a single drill, according to other example embodiments, a package may contain two or more drills. For instance, the drills may be arranged in parallel with each other, each one having a tool engaging portion held by a respective individual locking portion. For such a multi-drill package, the subportions of the protecting portion may be wider compared to the elongated legs illustrated in the drawings.

The invention claimed is:

1. A package for a drill, comprising:
   a drill;
   a protecting portion comprising a first subportion and a second subportion, the first subportion including a first segment and a second segment, the protecting portion being arranged to house a cutting portion of the drill in a contact free manner, and
   a locking portion arranged to hold a tool engaging portion of the drill, wherein the locking portion is movable relative to the second subportion and the first segment of the first subportion,
   wherein the drill being held by the locking portion is releasable from the locking portion by a movement of the locking portion and the second segment of the first subportion relative the second subportion and the first segment of the first subportion, wherein the first and the second subportions of the protecting portion are made in one piece and are arranged to allow the user to clamp the cutting portion of the drill by pressing the first segment of the first subportion towards the second subportion and thereby establishing a contact between the protecting portion and the cutting portion of the drill.

2. The package according to claim 1, wherein the protecting portion is made in one piece with the locking portion.

3. The package according to any one of claims 1-2, wherein the package is an inner package adapted to be sterilizable together with the drill.

4. The package according to any one of claims 1-2, wherein the movement of the locking portion relative the second subportion of the protecting portion and the first segment of the first subportion while the cutting portion of the drill is clamped results in the release of the tool engaging portion of the drill from the locking portion.

5. The package according to any one of claims 1-2, wherein at least one of the subportions of the protecting portion is made from a flexible material.

6. The package according to any one of claims 1-2, wherein the locking portion comprises a snap lock.

7. The package according to any one of claims 1-2, wherein the package is adapted such that the movement of the locking portion relative the second subportion of the protecting portion and the first segment of the first subportion may be achieved by bending.

8. The package according to any one of claims 1-2, wherein the package is adapted such that the relative movement between the locking portion, the second subportion of the protecting portion, and the first segment of the first subportion may be achieved by pivoting the locking portion (36) around an axis that is perpendicular to a longitudinal axis of the package.

9. The package according to any of claims 1-2, further comprising a gripping portion located adjacent the locking portion.

10. The package according to claim 9, wherein the package is adapted such that the relative movement between the locking portion, the second subportion of the protecting portion, and the first segment of the first subportion may be achieved by a movement of the gripping portion away from the longitudinal axis of the package.

* * * * *